United States Patent [19]

Tani et al.

[11] Patent Number: 5,272,036
[45] Date of Patent: Dec. 21, 1993

[54] PATTERN FORMING CONTRAST ENHANCED MATERIAL UTILIZING WATER SOLUBLE PHOTOSENSITIVE DIAZO COMPOUND AND PATTERN FORMING METHOD

[75] Inventors: Yoshiyuki Tani, Neyagawa; Masayuki Endo, Izumi; Kazufumi Ogawa, Hirakata; Fumiyoshi Urano; Masaaki Nakahata, both of Kawagoe, all of Japan

[73] Assignees: Matsushita Electronic Industrial Co., Ltd.; Wako Pure Chemical Industries, Ltd., Osaka, Japan

[21] Appl. No.: 860,209

[22] Filed: Mar. 27, 1992

Related U.S. Application Data

[63] Continuation of Ser. No. 427,398, Oct. 27, 1989, abandoned.

[30] Foreign Application Priority Data

Oct. 28, 1988 [JP] Japan .................. 63-272650

[51] Int. Cl.$^5$ .................. G03F 7/023; G03F 7/30
[52] U.S. Cl. .................. 430/191; 430/156; 430/158; 430/166; 430/192; 430/193; 430/325; 430/326; 430/945
[58] Field of Search .................. 430/191, 192, 193, 156, 430/158, 166, 326, 945, 325

[56] References Cited

U.S. PATENT DOCUMENTS 4,622,283 11/1986 Gray .................. 430/191
4,745,042 5/1988 Sasago et al. .................. 430/156
4,910,123 3/1990 Endo et al. .................. 430/326

FOREIGN PATENT DOCUMENTS 1-33543 2/1989 Japan.

OTHER PUBLICATIONS

B. F. Griffing et al., IEEE Electron Device Letters, vol. EDL-4, No. 1, Jan., pp. 14-16 (1983).
M. Sasago et al., 1985 Symposium on VLSI Technology, Digest Technical Papers, pp. 76-77 (1985).
M. Endo et al., Technical Papers in Regional Technical Conference on Photopolymers Principles Processes and Materials, Oct. 30-Nov. 2, pp. 39-50 (1988).
B. F. Griffing et al., 6th Int. Tech. Confr. on Photopolymer (by Polymer Engineering & Sci.), pp. 185-192.

Primary Examiner—Charles L. Bowers, Jr.
Assistant Examiner—Christopher G. Young
Attorney, Agent, or Firm—Armstrong, Westerman, Hattori, McLeland & Naughton

[57] ABSTRACT

Disclosed is a pattern forming contrast enhanced material comprising (a) a water soluble photosensitive compound selected from the group consisting of a water soluble aliphatic photosensitive compound (excluding ring compounds) having one or more of the group expressed by the formula (I), an aliphatic photosensitive quaternary ammonium salt having one or more of the group expressed by the formula (I), an aromatic photosensitive quaternary ammonium salt having one or more of the group expressed by the formula (I), and a photosensitive pyridinium salt having one or more of the group expressed by the formula (I), (b) a water soluble resin and (c) water and a pattern forming method using the same.

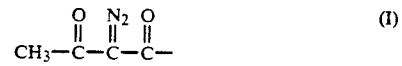

According to the present invention, this material is used as a contrast enhanced layer in the exposure effected by deep ultraviolet ray such as an excimer laser beam to form a good fine pattern of a submicron order.

20 Claims, 4 Drawing Sheets

PATTERN FORMING CONTRAST ENHANCED MATERIAL UTILIZING WATER SOLUBLE PHOTOSENSITIVE DIAZO COMPOUND AND PATTERN FORMING METHOD

This application is a continuation of application Ser. No. 07/427,398 filed Oct. 27, 1989, now abandoned.

BACKGROUND OF THE INVENTION

1. Field of the Invention

The present invention relates to a pattern forming contrast enhanced material. The present invention also relates to a pattern forming method. More specifically, the present invention relates to a pattern forming method using a contrast enhanced material having such properties that the material has a low primary transmittance to deep ultraviolet ray such as KrF excimer laser and the like, a bleaching action to these rays and an increased transmittance after the perfect bleaching.

2. Description of Related Art

The progress of the high density integration of a semiconductor integrated circuit has been carried out together with a conventional lithography technology and the smallest line width thereof is dashing in a region of submicron. The resolution R of lithography by a reduction projection method is expressed by the following Rayleigh's equation:

$$R = k_1 \times \lambda/NA \quad (1)$$

where
- $k_1$: process coefficient
- $\lambda$: wavelength
- NA: numerical aperture of lens From the above equation, a critical resolution is 0.68 μm and insufficient for submicron lithography, when using g-line (0.436 μm) and a stepper of NA of 0.45 and $k_1$ being 0.7.

Griffing et al. reported that by laminating a contrast enhanced layer for improving the contrast of the optical strength profile on the resist for pattern forming, a process coefficient $k_1$ can be decreased and a resolution and pattern profile can be improved (B. F. Griffing et al., IEEE ELECTRON DEVICE LETTERS, Vol. EDL-4, No. 1, Jan., pages 14–16 (1983).

According to their report, a resolution of 0.4 μm is possible in the ordinary reduction projecting method (λ: 0.436 μm, NA: 0.32).

Sasago et al. have found that the contrast enhanced material of Griffing et al. requires the formation of a water soluble interlayer thin film on a resist and hence not suitable for practical processes, since it contains an organic solvent, and reported a water soluble contrast enhanced material consisting of a water soluble resin and water soluble photosensitive compound (a diazonium salt) (M. Sasago et al., 1985 SYMPOSIUM ON VLST TECHNOLOGY, Digest of Technical Papers, pages 76–77 (1985).

This water soluble contrast enhanced material is bleached in a wavelength range of 365–406 nm by exposure. Also, since it is water soluble, it can be directly applied on a resist film without being mixed with the resist.

On the other hand, in order to reduce a wavelength of light source, a pattern forming method using KrF excimer laser beam of a wavelength of 248 nm is proposed. The wavelength can be reduced about by 40% by using KrF excimer laser instead of g-line. Therefore considering the above equation (1), it is expected that the resolution can be improved thereby.

Endo et al. reported the use of a compound having group in its molecule as a photosensitive compound in a pattern forming material for deep ultraviolet ray (M. Endo et al., Technical Papers in Regional Technical Conference on Photopolymers Principles Processes and Materials, Oct. 30–Nov. 2, pages 39–50 (1988). Since transmittance relatively greatly changes due to exposure to KrF excimer laser beam in this pattern forming material, it is expected to decrease a process coefficient. However, the change of transmittance is still insufficient for improving contrast and hence not always provide a good result. Also, since the pattern forming material is not water soluble, it is difficult to apply it to practical processes in the same way as the contrast enhanced material of Griffing et al. which requires the formation of a water soluble interlayer thin film.

Endo et al. also reported an excimer laser lithography using a water soluble contrast enhanced material (U.S. patent application Ser. No. 372,227). The contrast enhanced material in this report consists of a photosensitive compound having group in its molecule and a water soluble polymer. A —SO$_3$H group attached to an aromatic ring is selected as a water soluble group of the photosensitive compound. However, the —SO$_3$H group alone cannot provide an aromatic photosensitive compound having group in its molecule with enough water solubility. Therefore, it is difficult to dissolve the compound in pure water so that the primary transmittance may become sufficiently low and hence a good pattern formation is not expected.

Thus, there has been expected the lithography technology using a water soluble contrast enhanced material capable of decreasing a process coefficient and utilizing deep ultraviolet ray such as KrF excimer laser beam and the like.

SUMMARY OF THE INVENTION

The present inventors have found that the above problems can be solved by using a pattern forming contrast enhanced material comprising (a) a water soluble photosensitive compound selected from the group consisting of a water soluble aliphatic photosensitive compound (excluding ring compounds) having one or more of the group expressed by the following formula (I), an aliphatic photosensitive quaternary ammonium salt having one or more of the group expressed by the formula (I), an aromatic photosensitive quaternary ammonium salt having one or more of the group expressed by the formula (I), and a photosensitive pyridinium salt having one or more of the group expressed by the formula (I), (b) a water soluble resin and (c) water:

(I)

The present invention relates to a pattern forming contrast enhanced material comprising (a) a water soluble photosensitive compound selected from the group consisting of a water soluble aliphatic photosensitive compound (excluding ring compounds) having one or more of the group expressed by the formula (I), an aliphatic photosensitive quaternary ammonium salt having one or more of the group expressed by the formula (I), an aromatic photosensitive quaternary ammonium salt having one or more of the group expressed by the formula (I), and a photosensitive pyridinium salt having one or more of the group expressed by the formula (I), (b) a water soluble resin and (c) water.

Further, the present invention relates to a method of forming a pattern comprising (i) applying a pattern forming material on a substrate, (ii) forming a film of a pattern forming contrast enhanced material comprising (a) a water soluble photosensitive compound selected from the group consisting of a water soluble aliphatic photosensitive compound (excluding ring compounds) having one or more of the group expressed by the formula (I), an aliphatic photosensitive quaternary ammonium salt having one or more of the group expressed by the formula (I), an aromatic photosensitive quaternary ammonium salt having one or more of the group expressed by the formula (I), and a pyridinium salt having one or more of the group expressed by the formula (I), (b) a water soluble resin and (c) water, (iii) effecting exposure using a KrF excimer laser beam and (iv) effecting development.

(I)

An object of the present invention is to provide a pattern forming contrast enhanced material having a contrast effect to deep ultraviolet ray, in particular, to an excimer laser beam of 248 nm and a pattern forming method using this material.

Other objects and advantages of the present invention will be apparent from the following description when considered in connection with the accompanying drawings.

PREFERRED EMBODIMENTS OF THE INVENTION

A contrast enhanced material according to the present invention must be provided with the conditions that a resin to be used has less absorption around 248 nm, a photosensitive compound to be used has a transmittance around 248 nm which greatly increases after exposure, the material can be solved in aqueous solvent (e.g., an alkaline solution or the like as a developer for a resist) regardless of an optical reaction, and a solvent to be used has no absorption around 248 nm.

The inventors selected water soluble resins as the resins satisfying these requirements. The water soluble resins used in the present invention include pullulan, polyvinyl alcohol, polyvinyl pyrrolidone, polyethylene glycol, polyethylene oxide, water soluble cellulose derivatives such as sodium carboxymethyl cellulose, methyl cellulose, hydroxyethyl cellulose, hydroxypropyl cellulose, hydroxypropyl methyl cellulose and the like. They may be used independently or in the combination composed of two or more kinds thereof.

Note that although the above water soluble resins generally exhibit a transmittance of about ten percent at 248 nm when they are a thick film of 1.0 μm or more, they have a transmittance of several tens percent at 248 nm when they are a thin film of 0.5 μm or less. Therefore, when the contrast enhanced material according to the present invention is applied to a thickness of 0.5 μm on a resist for forming a pattern, a contrast enhanced effect can be obtained without causing any problem. In addition, these water soluble resins have an advantage to enable an $N_2$ gas to easily pass from an underlayer therethrough.

A compound having group is selected as a photosensitive compound in order to increase a ratio of a transmittance at around 248 nm before exposure to that after exposure.

More specifically, the compound having group has large absorption around 248 nm before exposure and almost no absorption around 248 nm due to the reaction of:

Water soluble aliphatic photosensitive compounds having one or more of group used in this invention include the compounds having a hydrophilic group such as —OH group, —$SO_3H$ group (which may be in the form of such as Na salt, K salt, $NH_4$ salt, etc.), —COOH group (which may be in the form of Na salt, K salt, NH₄ salt, etc.), an amino group, a substituted amino group, etc. or compounds which are in the form of quaternary ammonium salt or pyridinium salt by themselves. Substituted groups of the above substituted amino group includes methyl group, ethyl group, hydroxyethyl group or sulfopropyl group. Note that the two hydrogens of the amino group can be independently substituted by any of the above substituted groups, respectively.

Further, the following compounds, etc., for example, can be sufficiently used as the water soluble photosensitive compound in this invention since they are water soluble, although they do not particularly have the hydrophilic group or the hydrophilic bond.

Incidentally, when the water soluble aliphatic photosensitive compound is in the form of quaternary ammonium salt or pyridinium salt, the aliphatic photosensitive compound itself may be water-insoluble.

Note that if a benzene ring exists in the molecule, the absorption effected by the benzene ring around 250 nm lowers a transmittance after exposure and a sufficient bleaching action is difficult to be obtained.

Consequently, it is preferable that the pattern forming contrast enhanced material according to the present invention does not contain the benzene ring. On the other hand, a substituted phenyl group, a naphthyl group, a substituted naphthyl group or a pyridyl group has an absorption peak in a range of about 280 nm to 350 nm and thus has a less effect for the improvement of transmittance after exposure. Therefore, an aromatic Photosensitive compound having both a group mentioned above and one or more of the group expressed by the formula (I) can be used in the present invention if it has high solubility to water.

Then the inventors have selected the quaternary ammonium salt of the aromatic photosensitive compound and the pyridinium salt of the aromatic photosensitive compound as a compound having high solubility.

Substituted groups of the phenyl group and the naphthyl group include alkyl group having 1-10 carbon atoms such as methyl group, ethyl group, propyl group, a butyl group, etc., alkoxy group having 1-5 carbon atoms such as methoxy group, ethoxy group, propoxy group, butoxy group, etc., OH group, carboxyl group, sulfonic acid group, amino group, substituted amino groups, etc. Substituents of the substituted amino groups are the same as mentioned above.

The photosensitive compound used in the contrast enhanced material according to the present invention is generally produced by the following method.

↓ diazotization

↓ quaternization
(in the case of amino or pyridyl group as end group)

quaternary ammonium salt or pyridinium salt

More specifically, when a compound having a group expressed by hereinafter, referred to as compound A) is diazotized, a compound having the group can be easily obtained. In addition, when the obtained compound has a terminal amino or pyridyl group, it is treated by acid such as, for example, p-toluenesulfonic acid, methane sulfonic acid, etc. according to a common method to quantitatively obtain the quaternary ammonium salt or the pyridinium salt having the group.

A diazotizing reaction is usually carried out in such a manner that the compound A, 0.5 to 3 moles, preferably 0.8 to 1.5 moles per mole of the compound A of a diazotizing agent and 0.5 to 5 moles, preferably 0.8 to 1.5 moles per mole of the compound A of a base are reacted in a suitable reaction solvent at a temperature of −10° to 30° C., preferably −5° to 10° C. for 15 min. to 5 hours, preferably 1 to 2 hours.

As a reaction solvent used in the diazotizing reaction there can be used an alcohol such as ethanol, isopropanol, etc.; ether such as ethyl ether, isopropyl ether, tetrahydrofuran, etc.; a halogenated hydrocarbon such as methylene chloride, chloroform, carbon tetrachloride, 1,2-dichloroethane, etc.; a hydrocarbon such as n-hexane, cyclohexane, toluene, etc. As a diazotizing agent, there can be used p-toluenesulfonylazide, benzenesulfonylazide, 2-azide-3-ethylbenzothiazolium fluoroborate, etc., and as a base, there can be used an organic base such as piperidine, triethylamine, N-methylpyrrolidine, N-methylmorpholine, pyridine, diethylamine, etc.; an alcoholate such as NaOCH₃, NaOC₂H₅,

KOC(CH$_3$)$_3$, KOC$_2$H$_5$, etc.; and metal sodium, sodium hydride, potassium hydride, etc.

Since the methods of synthesizing the compound A are different depending on the kind of R when it is expressed by the formula:

the compound A can be suitably synthesized by a synthesizing method corresponding to the kind of R. In addition, the compound A is commercially available depending on the kind of R and thus in this case it can be used as it is or after it is suitably refined.

A synthesizing method of some of the concrete compounds will be briefly described below.

The pattern forming contrast enhanced material according to the present invention is produced in such a manner that 0.5 part by weight or more, preferably 1-3 parts by weight of a photosensitive material and 1 part of a water soluble resin are mixed with water and made to a solution having a concentration of 5-50% by weight.

Next, a pattern forming method using the pattern forming contrast enhanced material according to the present invention will be described with reference to FIG. 1.

Figure 1:
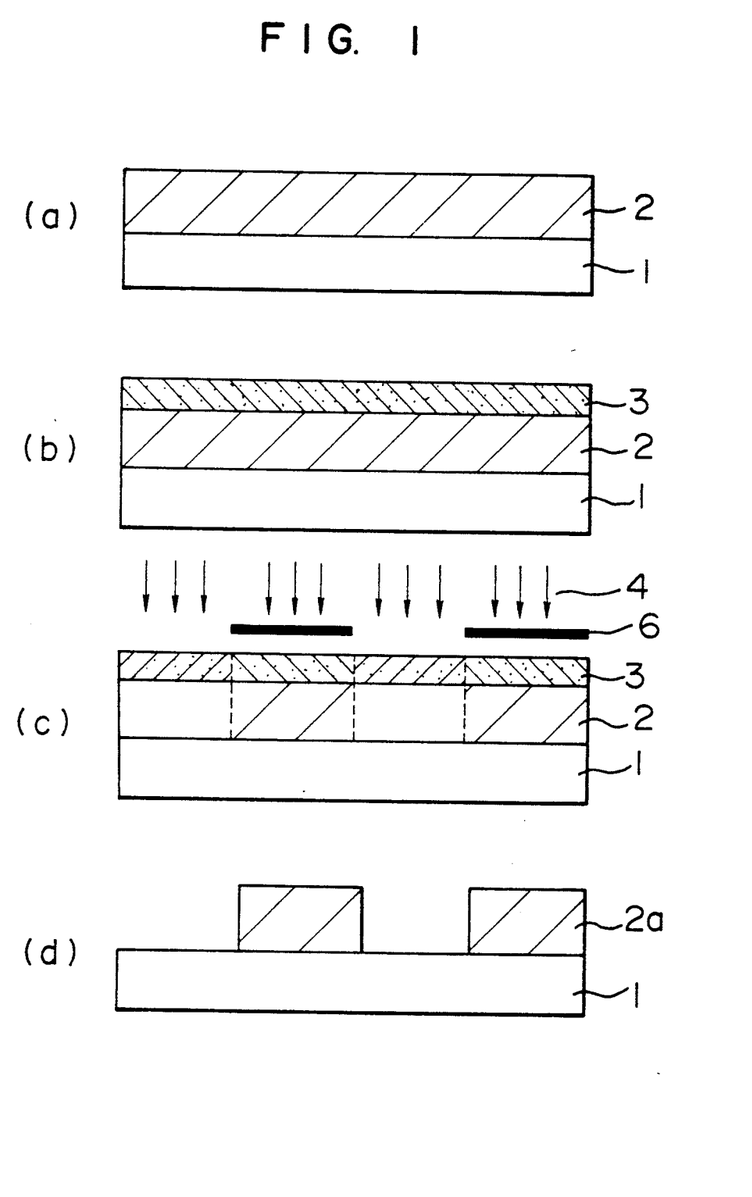
FIG. 1 is cross sectional views of a process of a pattern forming method using a pattern forming contrast enhanced material according to the present invention.

More specifically, for example, a suitable positive resist material 2 [e.g., MP2400 (made by Shipley Co., Inc.)] is spin-coated on a substrate 1 such as a silicon wafer and prebaked in an oven at 70° to 110° C. for 10 to 30 min. or on a hot plate at 70°-110° C. for 1-2 min. to obtain a resist film having a thickness of 0.5 to 2 μm [FIG. 1 (a)]. Note that the substrate 1 often has an oxide film, insulating film or conductive film formed thereon. Next, a contrast enhanced material 3 according to the present invention is spin-coated on the prebaked resist film 2 to a thickness of about 0.1-0.5 μm [FIG. 1 (b)]. Then, a mask 6 for obtaining a target pattern is held on the above resist film and a selective pattern exposure is effected by applying an excimer laser beam 4 of 248.4 nm having an exposure dose which is about 1.5 times that used when a pattern is formed using only an underlayer resist [FIG. 1 (c)]. Finally, it is developed for about 0.5-3 min. using a developer such as a water solution containing 20% of a 2401 developer (made by Shipley Co., Inc.) by a common method such as a dipping method, puddle method, spray method or the like with the result that the pattern forming contrast enhanced material layer 3 and the exposed portion of the pattern forming material 2 are solved and removed and thus the target pattern is formed on the substrate [FIG. 1 (d)].

Figure 4:
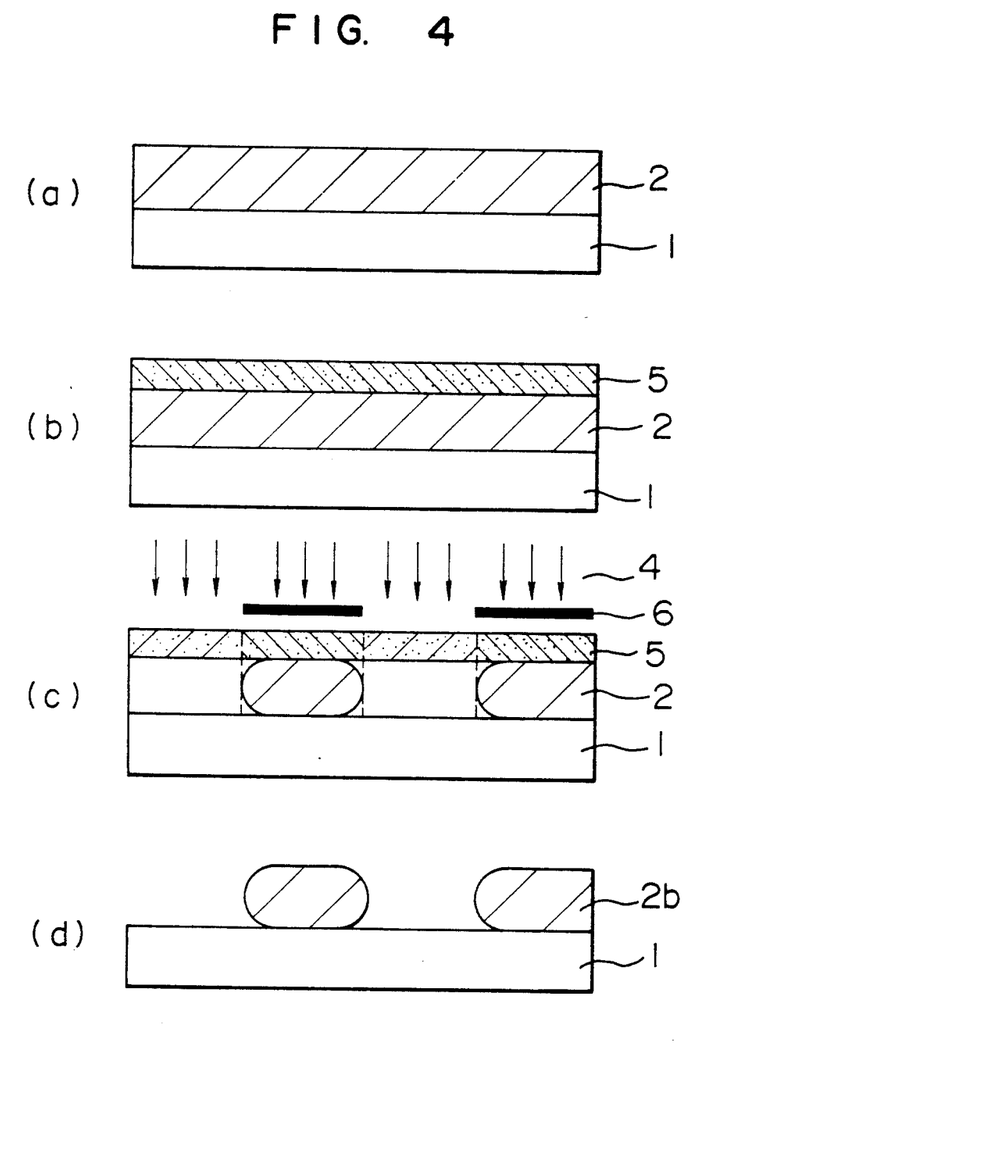
FIG. 4 is cross sectional views of a process of a pattern forming method using the conventional pattern forming contrast enhanced material.

FIG. 4 describes a method of forming a pattern by an excimer laser exposure using the conventional contrast enhanced material, wherein a resist 2 is spin-coated on a substrate 1 [FIG. 4 (a)]; a water soluble contrast enhanced layer 5 is formed by spin-coating on the resist 2 [FIG. 4 (b)]; and then an excimer laser beam 4 is selectively applied through a mask 6 by a reduced projection method [FIG. 4 (c)]. At the time, not only the contrast enhanced layer 5 but also a portion of the resist 2 are selectively irradiated. Finally, a usual developing process is carried out to remove the water soluble contrast enhanced layer 5 as well as only the portion of the resist 2 where the laser beam is applied whereby a pattern 2b is formed [FIG. 4 (d)].

Note that the positive resist materials include, for example, alkali soluble resins having good photo transmittance in the vicinity of 248.4 nm such as p-cresol novolac resins, m-cresol novolac resins, o-chloro-m-cresol novolac resins, maleimide resins, hydroxystyrene resins, poly(p-vinylphenol) resins, phenol resins, styrene resins, maleic acid resins, etc.

Further, the above resist material is usually used by being dissolved in an organic solvent. The organic solvents used for this object include, for example, diethylene glycol dimethylether, diethylene glycol diethylether, ethylcellosolve acetate, methylcellosolve acetate, etc. Said organic solvents, however, are not limited to them, but any solvent capable of dissolving a photosensitive compound and resin may be used.

In addition, it suffices to select as a developer used in the above pattern forming method an alkaline solution having a suitable concentration which does not almost dissolve an unexposed portion but dissolve an exposed portion in accordance with the solubility of the resin used as the resist material in the alkaline solution, and the concentration is usually selected from a range of 0.01 to 50%. The alkaline solutions used include solutions each containing an organic amine such as tetramethyl ammonium hydroxide (TMAH), etc. and inorganic alkali such as NaOH, KOH, etc.

The present invention will be described below more specifically referring to the following Examples. However, the present invention should not be construed to be restricted to the Examples.

Referential Example 1

Synthesis of 3,8-bis-diazo-2,4,7,9-decanetetraone

(1) Synthesis of 2,4,7,9-decanetetraone

To a suspension of sodium hydride (60% in oil, 15 g) in dry tetrahydrofuran (200 ml), a solution of 2,4-pentanedione (37.5 g, 0.375 mol) in dry tetrahydrofuran (100 ml) was added dropwise of $-5° \sim 0°$ C. with stirring under nitrogen, and the resultant mixture was stirred for 20 min. at the same temperature. To this suspension, n-butyllithium (1.6M in n-hexane solution, 250 ml) was added dropwise at the same temperature, followed by the addition of cuprous chloride (5.63 g) at $-10°$ C. or lower and the resultant mixture was stirred for 45 min. at $-5° \sim 0°$ C. Then to this suspension, iodine (47.6 g, 0.19 mol) in ethyl ether (250 ml) was added dropwise at $0° \sim 5°$ C., stirring was continued for 7 hrs. at room temperature and the resultant mixture was allowed to stand for overnight. The reaction mixture was poured into dilute hydrochloric acid, subjected to extraction with ethyl acetate, the organic layer was washed with $H_2O$ (200 ml×3), dried over anhydrous $MgSO_4$ and evaporated in vacuo. The resultant residue (22.5 g) was chromatographed on silica gel (Wako Gel C-200, manufactured by Wako Pure Chemical Industries, Ltd.) with dichloromethane as eluent, followed by recrystallization from cyclohexane to give the title compound as yellow leaflets which was an ca 1:1 mixture of Keto/Enol as seen by the methylene singlet at δ3.64 ppm and the methine singlet at δ5.53 ppm in a $^1$HNMR spectrum; yield: 8.2 g; mp 62.7°~64° C.

(2) Synthesis of 3,8-bis-diazo-2,4,7,9-decanetetraone

To a solution of 2,4,7,9-decanetetraone (7.9 g, 40 mmol) obtained in the above process (1) and piperidine (6.9 g, 80 mmol) in chloroform (200 ml), p-toluenesulfonylazide (15.8 g, 80 mmol) in chloroform (50 ml) was added dropwise at 3020 ~35° C., and stirring was continued for 2 hrs. at the same temperature. The reaction mixture was concentrated and the resultant residue was chromatographed on silica gel (Wako Gel C-200) with dichloromethane/ethyl acetate (10:1) as eluent to give the title compound as a yellow crystals; yield: 2.5 g; mp 79°~82.5° C.

Referential Example 2

Synthesis of 2-diazo-3-oxo-N,N-diethylbutyramide (1) Synthesis of 3-oxo-N,N-diethylbutyramide To a solution of diethylamine (35 g, 0.48 mol) in benzene (75 ml), diketene (40.2 g, 0.48 mol) in benzene (100 ml) was added dropwise at 20°~30° C., stirring was continued for 1 hr. under reflux, and evaporated. The residue (75 g) was chromatographed on silica gel (wako Gel C-200) with dichloromethane/ethyl acetate (10:1) as eluent to give the title compound as a yellow viscous oil; yield: 48.4 g.

(2) Synthesis of 2-diazo-3-oxo-N,N-diethylbutyramide

To a solution of 3-oxo-N,N-diethylbutyramide (11.8 g, 75 mmol) obtained in the above process (1) and triethylamine (7.6 g, 75 mmol) in acetonitrile (120 ml), p- toluenesulfonylazide (14.8 g, 75 mmol) in acetonitrile (20 ml) was added dropwise at 20°~25° C., and stirring was continued for 2.5 hrs. at the same temperature. The reaction mixture was concentrated under reduced pressure, diluted with ethyl ether (50 ml), washed with dilute aqueous potassium hydroxide and $H_2O$, dried over anhydrous $MgSO_4$ and evaporated under reduced pressure. The resultant residue (6.8 g) was chromatographed on silica gel (Wako Gel C-200) with dichloromethane/ethyl acetate (5:1) as eluent to give the title compound as a yellow viscous oil; yield: 2.4 g.

| | |
|---|---|
| $^1$HNMR δppm (CDCl$_3$): | 1.24(6H, t, J=8Hz, −N(CH$_2$CH$_3$)$_2$), 2.35(3H, s, CH$_3$CO—), 3.40(4H, q, J=8Hz, −N(CH$_2$CH$_3$)$_2$). |
| IR(Neat)νcm$^{-1}$: | 2100(>C=N$_2$), 1630(C=O). |
| UV(MeOH) λ$_{max}$nm(ε): | 227.8(12000). |
| Anal. calcd. for C$_8$H$_{13}$N$_3$O$_2$: | C %, 52.45; H %, 7.15; N %, 22.94. |
| Found: | C %, 52.51; H %, 7.01; N %, 22.75. |

Referential Example 3

Synthesis of 4-(2-diazo-1,3-dioxobutyl)pyridinium p-toluenesulfonate (1) synthesis of 4-(1,3-dioxobutyl)pyridine To a suspension of methyl isonicotinate (96.0 g, 0.7 mol) and sodium methoxide (45.4 g, 0.84 mol) in ethyl ether (1 l), acetone (81.3 g, 1.4 mol) was added dropwise at 25°~30° C. and stirring was continued for 2 hrs. under reflux. After cooling, acetic acid (50.4 g, 0.84 mol) was added to the reaction mixture, the organic layer was separated, washed twice with $H_2O$, dried over anhydrous $MgSO_4$ and evaporated. The residue (87.5 g) was distilled under reduced pressure to give the title compound as a pale yellow oil which solidified in the refrigerator; yield: 40.2 g; bp 135°~138° C./10 mmHg; mp 62°~64.5° C. (Lit. bp 118°~120° C.; mp 66.5°~67° C.; R. Levine, J. K. Sneed, J. Am. Chem. Soc., 73, 5614 (1951).).

$^1$HNMR δppm(CDCl$_3$): 2.23(3H, s, CH$_3$CO—), 6.23 (1H, s, −C$\underline{H}$=C—), 7.67(2H, dd, J=6Hz, Ar 3-H, 5-H),
 |
 OH
8.70(2H, dd, J=6Hz, Ar 2-H, 6-H), 15.00(1H, bs, −CH=C—).
 |
 O$\underline{H}$ (2) Synthesis of 4-(2-diazo-1,3-dioxobutyl)pyridine To a solution of 4-(1,3-dioxobutyl)pyridine (4.9 g, 30 mmol) obtained in the above process (1) and triethylamine (3.2 g, 31 mmol) in chloroform (75 ml), p-toluenesulfonylazide (6.3 g, 32 mmol) in chloroform (20 ml) was added dropwise at 10° C. or lower, and stirring was continued for 1.5 hrs. at the same temperature. The resultant solid was filtered off, the filtrate was washed twice with $H_2O$, dried over anhydrous $MgSO_4$ and evaporated in vacuo. The residue (7.1 g) was purified by silica gel column chromatography (Wako Gel C-200, manufactured by Wako Pure Chemical Industries, Ltd.) with dichloromethane/ethyl acetate (3:1) to give the title compound as a yellow crystals; yield: 3.5 g; mp 75.5°~76.5° C.

$^1$HNMR δppm (CDCl$_3$) 2.55 (3H, s, CH$_3$CO—), 7.50 (2H, dd, J=6Hz, Ar 3-H, 5-H), 8.80 (2H, dd, J=6Hz, Ar 2-H, 6-H).

IR (KBr) νcm$^{-1}$: 2120 (>C=N$_2$).

(3) Synthesis of 4-(2-diazo-1,3-dioxobutyl)pyridinium p-toluenesulfonate

To a solution of 4-(2-diazo-1,3-dioxobutyl)-pyridine (1.9 g, 10 mmol) obtained in the above process (2) in ethanol (30 ml), p-toluenesulfonic acid monohydrate (1.9 g, 10 mmol) in ethanol (20 ml) was added dropwise at 10°~15° C., the resultant mixture was continued for 1 hr. with stirring at room temperature and concentrated under reduced pressure. The resultant residue was recrystallized from isopropylalcohol to give the title compound as a yellow powders which was very hydroscopic; yield: 2.7 g; mp 106° C. (dec.).

$^1$HNMR δppm (CDCl$_3$—DMSO—d$_6$) 2.30 (3H, s, CH$_3$—), 2.40 (3H, s, CH$_3$CO—), 7.13 (2H, d, J=7Hz, phenyl 3-H, 5-H), 7.68 (2H, d, J=7Hz, phenyl 2-H, 6-H), 8.08 (2H, d, J=6Hz, pyridine 3-H, 5-H), 9.00 (2H, d, J=6Hz, pyridine 2-H, 6-H).

IR (KBr) νcm$^{-1}$: 2130 (>C=N$_2$).

Anal. calcd. for C$_{16}$H$_{15}$N$_3$O$_5$S: C%, 53.18; H%, 4.18; N%, 11.63.

Found: C%, 53.50; H%, 3.98; N%, 11.49.

Referential Example 4

Synthesis of 2-(2-diazo-1,3-dioxobutyl)pyridinium p-toluenesulfonate (1) Synthesis of 2-(1,3-dioxobutyl)pyridine Using ethyl picolinate (19.7 g, 0.13 mol) and sodium methoxide (8.6 g, 0.16 mol), the reaction was carried out in the same manner as described in Example 3(1), and residual oil (17.8 g) was distilled under reduced pressure to give the title compound as a yellow oil which was solidified in the refrigerator and which was an ca 1:3 mixture of Keto/Enol as seen by the methylene singlet at δ 4.27 ppm and the methine singlet at δ6.80 ppm in a $^1$HNMR spectrum; yield: 12.1 g; bp 143°~144° C./18 mmHg; mp 46°~49° C. (Lit. bp 114°~118° C./4.6 mmHg; mp 49°~50° C.; R. Levine, J. K. Sneed, J. Am. Chem. Soc., 73, 5614 (1951).).

$^1$HNMR δppm(CDCl$_3$): 2.20(3H, s, CH$_3$CO—), 4.27(2H, s, −COC$\underline{H_2}$CO—), 6.80(1H, s, −C=C$\underline{H}$—CO—),
 |
7.23~8.10(3H, m, Ar 3-H, 4-H, 5-H).
8.60(1H, d, J=7Hz, Ar 6-H), 15.45(1H, bs, −C=CH—).
 |
 O$\underline{H}$
IR(KBr)νcm$^{-1}$: 1630(>C=O).

(2) Synthesis of 2-(2-diazo-1,3-dioxobutyl)pyridine

Using 2-(1,3-dioxobutyl)pyridine (4.9 g, 30 mmol) obtained in the above process (1) and piperidine (2.6 g, 31 mmol), the reaction was carried out in the same manner as described in Example 3(2), and residual solid (9.0 g) was purified by silica gel column chromatography (Wako Gel C-200) with dichloromethane/ethyl acetate (5:1) as eluent and then by the recrystallization from ethanol to give the title compound as a yellow plates; yield: 2.1 g; mp 83.0°~84.5° C. (Lit. mp 83°~84° C.; R. Levine, J. K. Sneed, J. Am. Chem. Soc., 73, 5614 (1951).).

$^1$HNMR δppm (CDCl$_3$) 2.67 (3H, s, CH$_3$CO—), 7.33~8.13 (3H, m, Ar 3-H, 4-H, 5-H), 8.60 (1H, d, J=7Hz, Ar 6-H).

IR (KBr) υcm$^{-1}$: 2140 (>C=N$_2$), 1630 (C=O).

(3) Synthesis of 2-(2-diazo-1,3-dioxobutyl)pyridinium p-toluenesulfonate

Using 2-(2-diazo-1,3-dioxobutyl)pyridine (1.9 g, 10 mmol) obtained in the above process (2), the reaction was carried out in the same manner as described in Example 3(3), and residual solid was recrystallized from isopropylalcohol to give the title compound as a yellow powders which was very hydroscopic; yield: 2.2 g; mp 69°~74° C.

$^1$HNMR δppm (CDCl$_3$) 2.37 (3H, s, CH$_3$—), 2.63 (3H, s, CH$_3$CO—), 7.23 (2H, d, J=7Hz, phenyl 3-H, 5-H), 7.70 (2H, d, J=7Hz, phenyl 2-H, 6-H), 7.50~8.03 (3H, m, pyridine 3-H, 4-H, 5-H), 8.57 (1H, d, J=6Hz, pyridine 6-H).

IR (KBr) υcm$^{-1}$: 2180 (>C=N$_2$).

Anal. calcd. for C$_{16}$H$_{15}$N$_3$O$_5$S: C%, 53.18; H%, 4.18; N%; 11.63.

Found: C%, 53.29; H%, 3.89; N%, 11.54.

Referential Example 5

Synthesis of 2-Diazo-N-(2-hydroxyethyl)-3-oxobutanamide (1) Synthesis of N-(2-hydroxyethyl)-3-oxobutanamide To a solution of diketene (42.1 g, 0.5 mol) in dichloromethane (100 ml), ethanolamine (30.5 g, 0.5 mol) was added dropwise at 10°-20.C with stirring, and the reaction was carried out at room temperature for 2 hrs. After pouring H$_2$O (200 ml) into the reaction solution, an aqueous layer was separated, washed thrice with dichloromethane and was obtained N-(2-hydroxyethyl)-3-oxobutanamide as an aqueous solution.

(2) Synthesis of 2-Diazo-N-(2-hydroxyethyl)-3-oxobutanamide

In an aqueous solution of N-(2-hydroxyethyl)-3-oxobutanamide obtained in the above process (1), triethylamine (50.0 g, 0.5 ml) was dissolved, then p-toluenesulfonylazide (98.5 g, 0.5 mol) was added dropwise at 0°-10.C and the reaction was carried out at room temperature for 3 hrs. Then, the reaction mixture was extracted with dichloromethane (100 ml×3), the organic layer was dried over anhydrous MgSO$_4$ and evaporated in vacuo. The resultant residue (122 g) was chromatographed on silica gel (Wako Gel C-200 manufactured by Wako Pure Chemical Industries, Ltd.) with dichloromethane/methanol (20:1) as an eluent to give the title compound as pale yellow crystals; yield: 24.5 g; mp. 69.0°-70.0° C.

$^1$H—NMR δ ppm (CDCl$_3$): 2.23 (1H, bs, —OH), 2.36 (3H, s, CH$_3$—), 3.54 (2H, m, —NHCH$_2$—), 3.76 (2H, t, J=5 Hz, —CH$_2$CH$_2$OH, 8.50 (1H, bd, NH).

IR (KBr) υ cm$^{-1}$: 2140 (C=N$_2$), 1640 (C=O).

Anal. calcd. for C$_6$H$_9$N$_3$O$_3$: C%, 42.10; H%, 5.30; N%, 24.55.

Found: C%, 42.23; H%, 5.45; N%, 24.41

Example 1

A compound having the following composition was used as a pattern forming contrast enhanced material to form a pattern.

| | |
|---|---|
| $$CH_3-\underset{\underset{O}{\|}}{C}-\underset{\underset{N_2}{\|}}{C}-\underset{\underset{O}{\|}}{C}-CH_3$$ | 4.0 g |
| pullulan | 2.0 g |
| pure water | 20.0 g |

More specifically, a positive resist [MP-2400 (made by Shipley Co., Inc.)] was spin-coated on a semiconductor substrate and the substrate was prebaked at 90° C. on a hot plate for 2 min. to obtain a resist film having a thickness of 1.0 μm. Next, the pattern forming contrast enhanced material having the above composition according to the present invention was spin-coated on the resist film to have a thickness of 0.20 μm. Successively, a selective pattern exposure was effected through a mask using an excimer laser beam of 248.4 nm and finally development was effected using an ordinary alkaline developer (an aqueous solution containing 2.38% of TMAH) with the result that a pattern forming contrast enhanced material layer was removed, only the exposed portion of the pattern forming material was dissolved and removed to obtain a resist pattern. Note that this resist pattern was a submicron pattern of a good configuration having a pattern angle of 90°.

Figure 2:
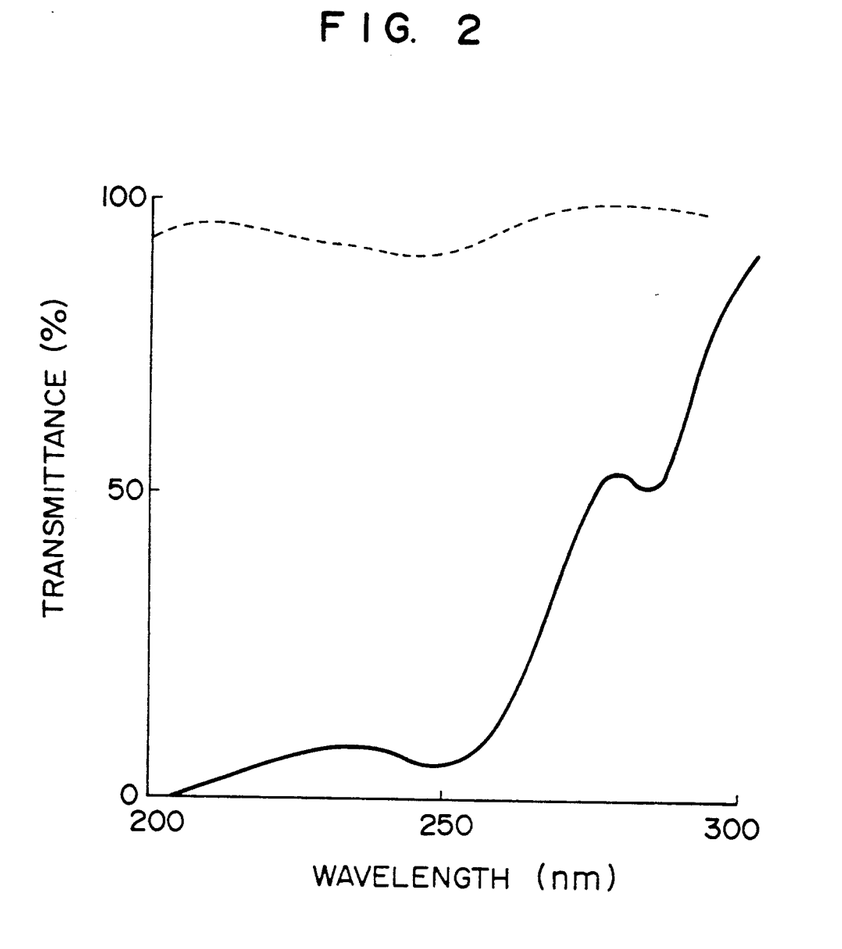
FIG. 2 is an ultraviolet spectroscopic spectrum of a pattern forming contrast enhanced material according to the present invention (a solid line shows the spectrum before exposure and a dotted line shows the spectrum after exposure)

As shown in FIG. 2 illustrating an ultraviolet spectroscopic curve of the pattern forming contrast enhanced material before and after the material was exposed, the transmittance of the material at 248 nm was greatly changed from 5% to 95% in the pre- and post-exposures.

Figure 3:
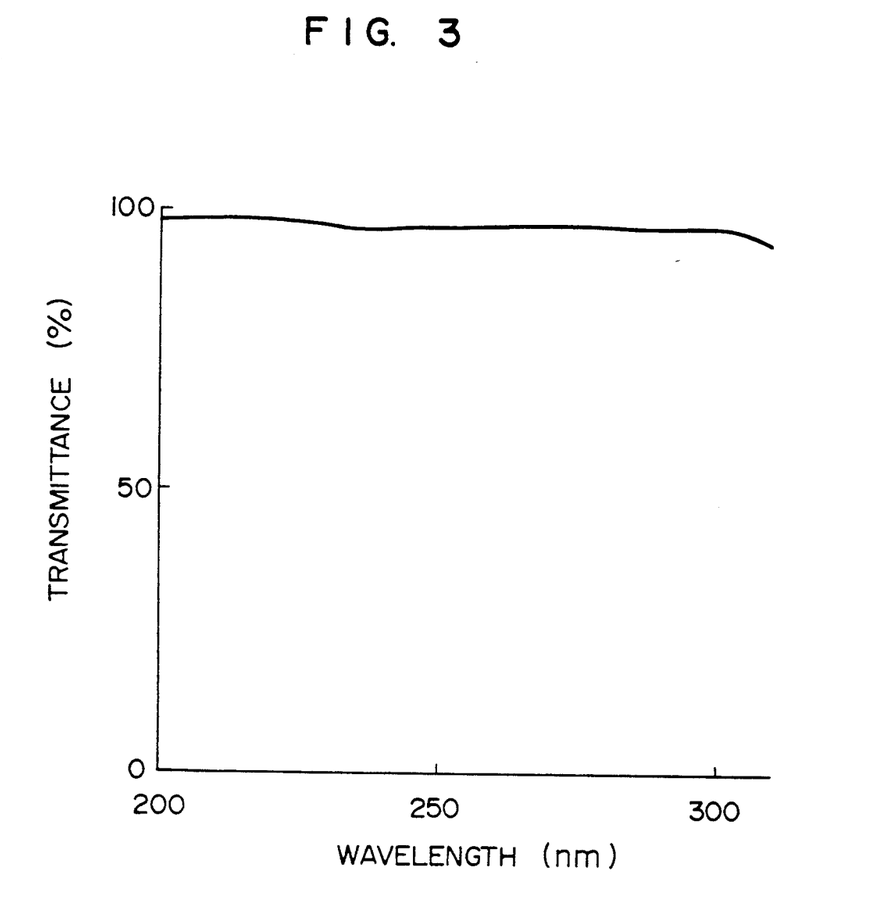
FIG. 3 is an ultraviolet spectroscopic spectrum of a conventional pattern forming contrast enhanced material.

In contrast, a conventional contrast enhanced material was suitable to ultraviolet ray of 436 nm, 365 nm or 406 nm but did not absorb deep ultraviolet ray, in particular, an excimer laser beam of 248 nm at all. Therefore, this material did not exhibit a contrast enhanced action at all to the exposure using the above excimer laser beam. It was found that no absorption was carried out in the deep ultraviolet ray region as apparent from an ultraviolet spectroscopic curve of a conventional contrast enhanced film (0.36 μm) shown in FIG. 3.

Example 2

A pattern forming contrast enhanced material having the following composition was produced and an experiment was carried out in the same manner as Example 1.

| | |
|---|---|
| $$CH_3-\underset{\underset{O}{\|}}{C}-\underset{\underset{N_2}{\|}}{C}-\underset{\underset{O}{\|}}{C}-N\diagup^{C_2H_5}_{C_2H_5}$$ | 4.0 g |
| (prepared in Referential Example 2) | |
| pullulan | 2.0 g |
| pure water | 20.0 g |

As a result, a good result similar to Example 1 was obtained.

Example 3

A pattern forming contrast enhanced material having the following composition was produced and an experiment was carried out in the same manner as Example 1.

| | |
|---|---|
| $CH_3-\underset{\underset{O}{\|\|}}{C}-\underset{\underset{N_2}{\|\|}}{C}-\underset{\underset{O}{\|\|}}{C}-OC_2H_5$ | 4.0 g |
| pullulan | 2.0 g |
| pure water | 20.0 g |

As a result, a good result similar to Example 1 was obtained.

Example 4

A pattern forming contrast enhanced material having the following composition was produced and an experiment was carried out in the same manner as Example 1.

| | |
|---|---|
| $\begin{array}{l}CH_2-\underset{\underset{O}{\|\|}}{C}-\underset{\underset{N_2}{\|\|}}{C}-\underset{\underset{O}{\|\|}}{C}-CH_3\\ \|\\ CH_2-\underset{\underset{O}{\|\|}}{C}-\underset{\underset{N_2}{\|\|}}{C}-\underset{\underset{O}{\|\|}}{C}-CH_3\end{array}$ (prepared in Referential Example 1) | 4.0 g |
| pullulan | 2.0 g |
| pure water | 20.0 g |

As a result, a good result similar to Example 1 was obtained.

Example 5

A pattern forming contrast enhanced material having the following composition was produced and an experiment was carried out in the same manner as Example 1.

| | |
|---|---|
| $CH_3-\underset{\underset{O}{\|\|}}{C}-\underset{\underset{N_2}{\|\|}}{C}-\underset{\underset{O}{\|\|}}{C}-(CH_2)_2-SO_3H$ | 4.0 g |
| pullulan | 2.0 g |
| pure water | 20.0 g |

As a result, a good result similar to Example 1 was obtained.

Example 6

A pattern forming contrast enhanced material having the following composition was produced and an experiment was carried out in the same manner as Example 1.

| | |
|---|---|
| $CH_3-\underset{\underset{O}{\|\|}}{C}-\underset{\underset{N_2}{\|\|}}{C}-\underset{\underset{O}{\|\|}}{C}-NH_2$ | 4.0 g |
| pullulan | 2.0 g |
| pure water | 20.0 g |

As a result, a good result similar to Example 1 was obtained.

Example 7

A pattern forming contrast enhanced material having the following composition was produced and an experiment was carried out in the same manner as Example 1.

| | |
|---|---|
| $CH_3-\underset{\underset{O}{\|\|}}{C}-\underset{\underset{N_2}{\|\|}}{C}-\underset{\underset{O}{\|\|}}{C}-CH_2-\overset{\oplus}{N}H_3 \; CH_3-CH_2-SO_3^{\ominus}$ | 4.0 g |
| pullulan | 2.0 g |
| pure water | 20.0 g |

As a result, a good result similar to Example 1 was obtained.

A pattern forming contrast enhanced material having the following composition was produced and an experiment was carried out in the same manner as Example 1.

| | |
|---|---|
| $CH_3-\underset{\underset{O}{\|\|}}{C}-\underset{\underset{N_2}{\|\|}}{C}-\underset{\underset{O}{\|\|}}{C}-CH-\overset{\oplus}{N}H_3 \; CH_3-\bigcirc-SO_3^{\ominus}$ | 4.0 g |
| pullulan | 2.0 g |
| pure water | 20.0 g |

As a result, a good result similar to Example 1 was obtained.

Example 9

A pattern forming contrast enhanced material having the following composition was produced and an experiment was carried out in the same manner as Example 1.

| | |
|---|---|
| $CH_3-\underset{\underset{O}{\|\|}}{C}-\underset{\underset{N_2}{\|\|}}{C}-\underset{\underset{O}{\|\|}}{C}-CH_2-\overset{\oplus}{N}H_3 \; CH_3-\bigcirc(CH_3)-SO_3^{\ominus}$ | 4.0 g |
| pullulan | 2.0 g |
| pure water | 20.0 g |

As a result, a good result similar to Example 1 was obtained.

Example 10

A pattern forming contrast enhanced material having the following composition was produced and an experiment was carried out in the same manner as Example 1.

| | |
|---|---|
| $CH_3-\underset{\underset{O}{\|\|}}{C}-\underset{\underset{N_2}{\|\|}}{C}-\underset{\underset{O}{\|\|}}{C}-CH_2-\overset{\oplus}{N}H_3 \; CH_3-\bigcirc-SO_3^{\ominus}$ | 4.0 g |
| pullulan | 2.0 g |
| pure water | 20.0 g |

As a result, a good result similar to Example 1 was obtained.

Example 11

A pattern forming contrast enhanced material having the following composition was produced and an experiment was carried out in the same manner as Example 1.

4.0 g pullulan 2.0 g
pure water 20.0 g

As a result, a good result similar to Example 1 was obtained.

Example 12

A pattern forming contrast enhanced material having the following composition was produced and an experiment was carried out in the same manner as Example 1.

4.0 g pullulan 2.0 g
pure water 20.0 g

As a result, a good result similar to Example 1 was obtained.

Example 13

A pattern forming contrast enhanced material having the following composition was produced and an experiment was carried out in the same manner as Example 1.

4.0 g pullulan 2.0 g
pure water 20.0 g

As a result, a good result similar to Example 1 was obtained.

Example 14

A pattern forming contrast enhanced material having the following composition was produced and an experiment was carried out in the same manner as Example 1.

4.0 g pullulan 2.0 g

-continued pure water 20.0 g

As a result, a good result similar to Example 1 was obtained.

Example 15

A pattern forming contrast enhanced material having the following composition was produced and an experiment was carried out in the same manner as Example 1.

4.0 g pullulan 2.0 g
pure water 20.0 g

As a result, a good result similar to Example 1 was obtained.

Example 16

A pattern forming contrast enhanced material having the following composition was produced and an experiment was carried out in the same manner as Example 1.

4.0 g pullulan 2.0 g
pure water 20.0 g

As a result, a good result similar to Example 1 was obtained.

Example 17

A pattern forming contrast enhanced material having the following composition was produced and an experiment was carried out in the same manner as Example 1.

4.0 g pullulan 2.0 g
pure water 20.0 g

As a result, a good result similar to Example 1 was obtained.

Example 18

A pattern forming contrast enhanced material having the following composition was produced and an experiment was carried out in the same manner as Example 1.

pullulan 4.0 g
pure water 2.0 g

As a result, a good result similar to Example 1 was obtained.

Example 19

A pattern forming contrast enhanced material having the following composition was produced and an experiment was carried out in the same manner as Example 1.

pullulan 2.0 g
pure water 20.0 g

As a result, a good result similar to Example 1 was obtained.

Example 20

A pattern forming contrast enhanced material having the following composition was produced and an experiment was carried out in the same manner as Example 1.

pullulan 2.0 g
pure water 20.0 g

As a result, a good result similar to Example 1 was obtained.

Example 21

A pattern forming contrast enhanced material having the following composition was produced and an experiment was carried out in the same manner as Example 1.

pullulan 2.0 g
pure water 20.0 g

As a result, a good result similar to Example 1 was obtained.

Example 22

A pattern forming contrast enhanced material having the following composition was produced and an experiment was carried out in the same manner as Example 1.

pullulan 2.0 g
pure water 20.0 g

As a result, a good result similar to Example 1 was obtained.

Example 23

A pattern forming contrast enhanced material having the following composition was produced and an experiment was carried out in the same manner as Example 1.

pullulan 2.0 g
pure water 20.0 g

As a result, a good result similar to Example 1 was obtained.

Example 24

A pattern forming contrast enhanced material having the following composition was produced and an experiment was carried out in the same manner as Example 1.

pullulan 2.0 g
pure water 20.0 g

As a result, a good result similar to Example 1 was obtained.

Example 25

A pattern forming contrast enhanced material having the following composition was produced and an experiment was carried out in the same manner as Example 1.

4.0 g

| pullulan | 2.0 g |
|---|---|
| pure water | 20.0 g |

As a result, a good result similar to Example 1 was obtained.

Example 26

A pattern forming contrast enhanced material having the following composition was produced and an experiment was carried out in the same manner as Example 1.

4.0 g

| pullulan | 2.0 g |
|---|---|
| pure water | 20.0 g |

As a result, a good result similar to Example 1 was obtained.

Example 27

A pattern forming contrast enhanced material having the following composition was produced and an experiment was carried out in the same manner as Example 1.

4.0 g

| pullulan | 2.0 g |
|---|---|
| pure water | 20.0 g |

As a result, a good result similar to Example 1 was obtained.

Example 28

A pattern forming contrast enhanced material having the following composition was produced and an experiment was carried out in the same manner as Example 1.

4.0 g

| pullulan | 2.0 g |
|---|---|
| pure water | 20.0 g |

As a result, a good result similar to Example 1 was obtained.

Example 29

A pattern forming contrast enhanced material having the following composition was produced and an experiment was carried out in the same manner as Example 1.

4.0 g

(prepared in Referential Example 4)

| pullulan | 2.0 g |
|---|---|
| pure water | 20.0 g |

As a result, a good result similar to Example 1 was obtained.

Example 30

A pattern forming contrast enhanced material having the following composition was produced and an experiment was carried out in the same manner as Example 1.

4.0 g

| pullulan | 2.0 g |
|---|---|
| pure water | 20.0 g |

As a result, a good result similar to Example 1 was obtained.

Example 31

A pattern forming contrast enhanced material having the following composition was produced and an experiment was carried out in the same manner as Example 1.

pullulan 2.0 g
pure water 20.0 g

As a result, a good result similar to Example 1 was obtained.

Example 32

A pattern forming contrast enhanced material having the following composition was produced and an experiment was carried out in the same manner as Example 1.

pullulan 2.0 g
pure water 20.0 g

As a result, a good result similar to Example 1 was obtained.

Example 33

A pattern forming contrast enhanced material having the following composition was produced and an experiment was carried out in the same manner as Example 1.

pullulan 2.0 g
pure water 20.0 g

As a result, a good result similar to Example 1 was obtained.

Example 34

A pattern forming contrast enhanced material having the following composition was produced and an experiment was carried out in the same manner as Example 1.

pullulan 2.0 g
pure water 20.0 g

As a result, a good result similar to Example 1 was obtained.

Example 35

A pattern forming contrast enhanced material having the following composition was produced and an experiment was carried out in the same manner as Example 1.

pullulan 2.0 g
pure water 20.0 g

As a result, a good result similar to Example 1 was obtained.

Example 36

A pattern forming contrast enhanced material having the following composition was produced and an experiment was carried out in the same manner as Example 1.

pullulan 2.0 g
pure water 20.0 g

As a result, a good result similar to Example 1 was obtained.

Example 37

A pattern forming contrast enhanced material having the following composition was produced and an experiment was carried out in the same manner as Example 1.

| | |
|---|---|
| $$CH_3-\overset{O}{\underset{\|}{C}}-\overset{N_2}{\underset{\|}{C}}-\overset{O}{\underset{\|}{C}}-OH$$ | 4.0 g |
| pullulan | 2.0 g |
| pure water | 20.0 g |

As a result, a good result similar to Example 1 was obtained.

Example 38

A pattern forming contrast enhanced material having the following composition was produced and an experiment was carried out in the same manner as Example 1.

| | |
|---|---|
| $$CH_3-\overset{O}{\underset{\|}{C}}-\overset{N_2}{\underset{\|}{C}}-\overset{O}{\underset{\|}{C}}-CH_2-COOH$$ | 4.0 g |
| pullulan | 2.0 g |
| pure water | 20.0 g |

As a result, a good result similar to Example 1 was obtained.

Although the present invention is described using only the pluran as the water soluble resin, water soluble resin applicable to the pattern forming contrast enhanced material according to the present invention is not limited to the pullulan and the same good result was obtained when polyvinyl alcohol, polyvinyl pyrrolidone, polyethylene glycol, polyethylene oxide, water soluble cellulose derivatives, etc. were used. In addition, although the pure water was used as a solvent, it is not limited to the pure water.

Example 39

A pattern forming contrast enhanced material having the following composition was produced and an experiment was carried out in the same manner as Example 1.

| | |
|---|---|
| $$CH_3-\overset{O}{\underset{\|}{C}}-\overset{N_2}{\underset{\|}{C}}-\overset{O}{\underset{\|}{C}}-NHCH_2CH_2OH$$ (prepared in Referential Example 5) | 4.0 g |
| pullulan | 2.0 g |
| pure water | 20.0 g |

As a result, a good result similar to Example 1 was obtained.

Example 40

A pattern forming contrast enhanced material having the following composition was produced and an experiment was carried out in the same manner as Example 1.

| | |
|---|---|
| $$CH_3-\overset{O}{\underset{\|}{C}}-\overset{N_2}{\underset{\|}{C}}-\overset{O}{\underset{\|}{C}}-OCH_2CH_2OH$$ | 4.0 g |
| pullulan | 2.0 g |
| pure water | 20.0 g |

As a result, a good result similar to Example 1 was obtained.

What is claimed is:

1. A contrast enhancing material for pattern forming comprising the following ingredients in admixture: (a) from 1 to 3 parts by weight of a water soluble photosensitive compound selected from the group consisting of a water soluble aliphatic photosensitive compound (excluding ring compounds) having one or more of the group expressed by the formula (I), an aliphatic photosensitive quaternary ammonium salt having one or more of the group expressed by the formula (I), an aromatic photosensitive quaternary ammonium salt having one or more of the group expressed by the formula (I), and a photosensitive pyridinium salt having one or more of the group expressed by the formula I; (b) 1 part by weight of a water soluble resin; and (c) water:

2. A pattern forming contrast enhanced material according to claim 1, wherein said water soluble photosensitive compound is selected from the group consisting of and 3. A pattern forming contrast enhanced material according to claim 1, wherein said water soluble photosensitive compound is an aliphatic photosensitive compound having both one or more of the group expressed by the formula (I) and —OH group.

4. A pattern forming contrast enhanced material according to claim 1, wherein said water soluble photosensitive compound is an aliphatic photosensitive compound having both one or more of the group expressed by the formula (I) and —SO$_3$H group.

5. A pattern forming contrast enhanced material according to claim 1, wherein said water soluble photosensitive compound is an aliphatic photosensitive compound having both one or more of the group expressed by the formula (I) and —COOH group.

6. A pattern forming contrast enhanced material according to claim 1, wherein said water soluble photosensitive compound is an aliphatic photosensitive compound having both one or more of the group expressed by the formula (I) and an amino group or substituted amino group.

7. A pattern forming contrast enhanced material according to claim 6, wherein the substituted group of said substituted amino group is at least one selected from the group consisting of methyl group, ethyl group, hydroxyethyl group and sulfopropyl group.

8. A pattern forming contrast enhanced material according to claim 1, wherein said water soluble photosensitive compound is an aliphatic or aromatic photosensitive quaternary ammonium salt having one or more of the group expressed by the formula (I).

9. A pattern forming contrast enhanced material according to claim 1, wherein said water soluble photosensitive compound is a photosensitive pyridinium salt having one or more of the group expressed by the formula (I).

10. A pattern forming contrast enhanced material according to claim 1, wherein said water soluble resin is at least one selected from the group consisting of pullulan, polyvinyl alcohol, polyvinyl pyrrolidone, polyethylene glycol, polyethylene oxide and water soluble cellulose derivatives.

11. A pattern forming method, comprising
(i) applying a pattern forming material on a substrate;
(ii) forming a film of a pattern forming contrast enhancing material on said pattern forming material, said pattern forming contrast enhancing material comprising the following ingredients in admixture:
(a) from 1 to 3 parts by weight of a water soluble photosensitive compound selected from the group consisting of a water soluble aliphatic photosensitive compound (excluding ring compounds) having one or more of the group expressed by the formula (I), an aliphatic photosensitive quaternary ammonium salt having one or more of the group expressed by the formula (I), an aromatic photosensitive quaternary ammonium salt having one or more of the group expressed by the formula (I), and a photosensitive pyridinium salt having one or more of the group expressed by the formula (I); (b) 1 part by weight of a water soluble resin; and (c) water;

(I)

(iii) effecting imagewise exposure using a KrF excimer laser beam; and
(iv) effecting development using an aqueous alkaline solution
to remove all the contrast enhancing material and the soluble non-image portion of the pattern forming material.

12. A pattern forming method according to claim 11, wherein said water soluble photosensitive compound is selected from the group consisting of and 13. A pattern forming method according to claim 11, wherein said water soluble photosensitive compound is an aliphatic photosensitive compound having both one or more of the group expressed by the formula (I) and —OH group.

14. A pattern forming method according to claim 11, wherein said water soluble photosensitive compound is an aliphatic photosensitive compound having both one or more of the group expressed by the formula (I) and —SO$_3$H group.

15. A pattern forming method according to claim 11, wherein said water soluble photosensitive compound is an aliphatic photosensitive compound having both one or more of the group expressed by the formula (I) and —COOH group.

16. A pattern forming method according to claim 11, wherein said water soluble photosensitive compound is an aliphatic photosensitive compound having both one or more of the group expressed by the group formula (I) and an amino group or a substituted amino group.

17. A pattern forming method according to claim 16, wherein the substituted group of said substituted amino group is at least one selected from the group consisting of methyl group, ethyl group, hydroxyethyl group and sulfopropyl group.

18. A pattern forming method according to claim 11, wherein said water soluble photosensitive compound is an aliphatic or aromatic photosensitive quaternary ammonium salt having one or more of the group expressed by the formula (I).

19. A pattern forming method according to claim 11, wherein said water soluble photosensitive compound is a photosensitive pyridinium salt having one or more of the group expressed by the formula (I).

20. A pattern forming method according to claim 11, wherein said water soluble resin is at least one selected from the group consisting of pullulan, polyvinyl alcohol, polyvinyl pyrrolidone, polyethylene glycol, polyethylene oxide and water soluble cellulose derivatives.

* * * * *